United States Patent [19]
Zhang et al.

[11] Patent Number: 5,616,604
[45] Date of Patent: Apr. 1, 1997

[54] AMINOPYRROLIZINONE ANALOGUES FOR ANTI-INFLAMMATION AND ANALGESIA (II)

[76] Inventors: Shoufang Zhang; Xinxian Zhao; Wenfang Kao; Jinrui Wang, all of 67-08 168th St., Flushing, N.Y. 11365

[21] Appl. No.: 600,891

[22] Filed: Feb. 15, 1996

[51] Int. Cl.$^6$ .......................... A61K 31/40; C07D 487/02
[52] U.S. Cl. ............................................. 514/413; 548/512
[58] Field of Search .............................. 514/413; 548/512

[56] References Cited

PUBLICATIONS

CA88: 190517m Diastereomeric . . . heterocycles. Filira et al., p. 735, 1978.

*Primary Examiner*—Joseph McKane
*Attorney, Agent, or Firm*—Shoufang Zhang; Xinxian Zhao; Wenfang Kao

[57] ABSTRACT

New pharmaceutical compounds, which are novel aminopyrrolizinone analogues, having anti-inflammatory and analgesic function and method of making the same.

3 Claims, No Drawings

AMINOPYRROLIZINONE ANALOGUES FOR ANTI-INFLAMMATION AND ANALGESIA (II)

BACKGROUND OF THE INVENTION

This present invention relates to novel aminopyrrolizinone derivatives and method of making the same. The novel aminopyrrolizinones have significant analgesic and anti-inflammatory activity and low toxicity.

DESCRIPTION OF PRIOR ART

A lot of pharmaceutical compounds have analgesic and anti-inflammatory activities. For example, ibuprofen has been made available without prescription in the U.S. and other countries. It is standard over-the-counter analgesic drug (i.e. aspirin or paracetamol) in many conditions. Ibuprofen possessed anti-inflammatory activity and used for treatment of arthritic disorders. However, ibuprofen caused gastric irritation, and skin rashes. Ibuprofen-induced pseudo-pelger-huet anomaly has been described. The abnormality was part of a sensitivity reaction characterized by diffuse pruritic maculopapule, fever, vomiting and diarrhea. Other example, indomethacin as anti-inflammatory and analgesic compound is widely used in osteoarthritis, rheumatoid disease, to reduce pain and inflammation. But indomethacin may cause gastrointestinal toxicity. Florence et al, reported that indomethacin displayed unusually adherent properties. More serious, indomethacin and related compounds also act as a vasoconstrictor of cerebral circulation, decreasing cerebral blood flow by 25–35% and abolishing cerebral blood flow response to hypercapnia. It also diminishes blood flow in the splanchnic vascular bed by increasing local vascular resistance. Some reports provide more evidences that indomethacin and related compounds impairs basal and stimulated blood flow by exerting a direct action on the resistance vessels of various regions, probably independent of its action on prostaglandin formation. Additionally, indomethacin can exacerbate the skin manifestations of dermatitis herpetiformis.

As mentioned above, so far, there obviously still lacks any effective anti-inflammatory and analgesic drugs, and at the same time there is nothing to do with the side effect.

The present invention relates novel aminopyrrolizinone derivatives, which show significant anti-inflammatory and analgesic activities. For example, compound Z-47 is more safe than ibuprofen and indomethacin. Also analgesic activity of Z-47 was stronger than indomethacin and ibuprofen.

DETAILED DESCRIPTION

This invention relates to aminopyrrolizinone analogues and their preparation.

The compounds of this invention have the general formula:

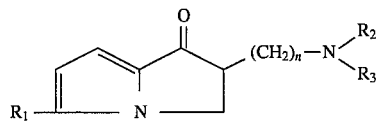
(I)

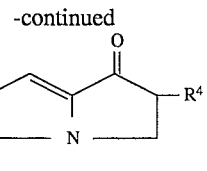
(II)

wherein n is 1–3.

wherein $R_1$ is H, or substituted benzoyl group:

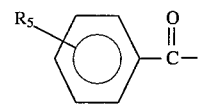

wherein $R_5$ is one of the following atoms or groups: H, F, Cl, Br, OH. —COOHCH$_3$COO—, H$_2$N—, CH$_3$CONH—, alkoxy group of 1–3 carbon atoms or alkoyxy group of 1–4 carbon atoms. The group locates at ortho, meta or para-position.

$R_2$ is the following atom or group: H or an alkyl group of 1 to 3 carbon atoms, or a substituted phenyl group;

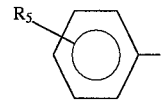

wherein $R_3=R_1$ or $R_2$ defined above or —(CH$_2$)n—R$_2$:n= 4–5.

wherein $R_4$ is H, substituted benzyl or benzylidene group:

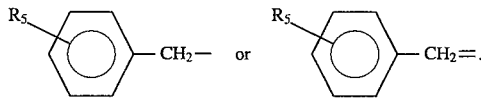

All the compounds above can be their organic or inorganic salts, for examples, hydrochloride, citrate, or sulfate.

The following compounds are taken as examples of the preferred compounds of this invention:

2-dimethylaminomethyl-1, 2-dihydro-1-pyrrolizinone.

5-benzoyl-2-dimethylaminomethyl-1, 2-dihydro-1-pyrrolizinone.

5-(4-chlorobenzoyl)-2-dimethylaminomethyl-1, 2-dihydro-1-pyrrolizinone.

2-N-pyrrolidinylmethyl-1, 2-dihyro-1-pyrrolizinone.

2-(3-methoxyphenylamino)methyl-1, 2-dihydro-1-pyrrolizinone.

2-(4-methlphenylamino)methyl-1, 2-dihyro-1-pyrrolizinone.

5-benzoyl-2-(4-ethoxyphenylamino)methyl-1, 2-dihydro-1-pyrrolizinone.

2-diethylaminomethyl-5-(3-methozybenzoyl)-1, 2-dihydro-1-pyrrolizinone.

5-acetyl-2-dimethylaminomethyl-1, 2-dihydro-1-phrrolizinone.

2-(4-acetylaminophenylamino)methyl-1, 2-dihydro-1-pyrrolizinone.

2-(4-ethoxyphenylamino)methyl-1, 2-dihydro-1-pyrrolizinone.

5-(4-methylphenylamino)methyl-1, 2-dihydro-1-pyrrolizinone.

2-(2-dimethylaminoethyl)-1, 2-dihydro-1-pyrrolizinone.

The compounds of formula (III) and (IV) can be prepared, according to the following process: reacting 1, 2-dihydro- 1-pyrrolizinone with formaldehyde and an amine:

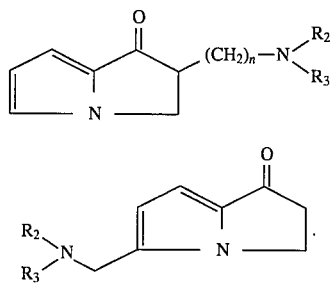

Formula III can react with KCN or CH₂CN to produce a nitrile, which was reduced, and then N-alkylated to afford compound III¹ or III².

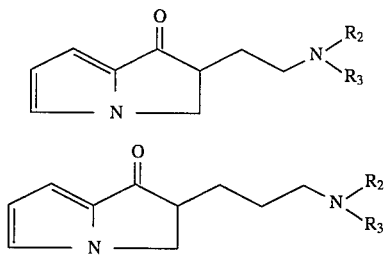

1, 2-dihydro-1-pyrrolizinone reacts with an acetyl chloride and a lewis acid or with an amide and phosphorus oxychloride to produce an acetyl-1, 2-dihydro-1-pyrrolizinone (V):

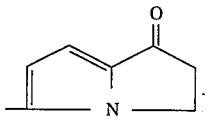

The compounds of formula (I) can be prepared from the compounds of formula (V). Compounds of formula (II) can be prepared from compounds of formula (IV). Compounds of formula (II) can also be prepared from compounds of formula (VI).

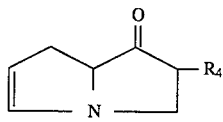

wherein the R groups of formula (III), (III¹), (III²), (IV), (V) and (VI) are defined as mentioned above. Compounds of formula (VI) can be prepared from 1, 2-dihydro-1-pyrrolizinone.

Examples of the preparation.

The HNMR spectra were measured by a Bruker-AC(E)-250 instrument using TMS as internal reference. The melting points were uncorrected.

EXAMPLE 1

1, 2-dihydro-1-pyrrolizinone (1).

To a solution of 10 g N-cyanoethylpyrrole in 100 ml ether was added 2.5 g ZnCl₂. Dried HCl was passed into the mixture at 5°–10° C. After 2 hours, the reaction mixture was allowed to stand at room temperature for 4 hours. Removed the solvent by suction, 20%. Aqueous NaOH was added until pH 3. The mixture was stirred at 80°–90° C. for 2 hours. Extracted with methylene chloride, dried over Na₂SO₄, evaporated the solvent, 8 g yellow solid was obtained. The crude product was crystallized from petroleum ether, 6.5 g compound (1) was obtained, as white crystals, mp 53°–54.5° C., yield 65%.

EXAMPLE 2

2-dimethylaminomethyl-1, 2-dihydro-1-pyrrolizinone (2).

To a mixture of 9 g 1, 2-dihydro-1-pyrrolizinone (1), 4.5 g paraformaldehyde and 12 g of dimethylamine chloride in 200 ml ethanol was added concentrated HCl until the mixture reached pH4. The mixture was refluxed for 12 hours. Evaporated most of the solvent, the residue allowed to stand at 0° C. 10 g yellow crystal was obtained. Recrystallized with ethanol, 9 g of (2) was obtained as chloride, mp 164°–165° C., yield 52%.

¹HNMR (D₂O), δ3.02 (S, 6H), 3.53 (m, 1H), 3.70 (m, 1H), 3.82 (m, 1H), 4.15 (dd, 1H), 4.67–4.75 (m, 1H), 6.66 (S, 1H), 6.87 (m, 1H), 7.35 (m, 1H).

EXAMPLE 3

5-(4-chlorobenzoyl)-1, 2-dihydro-1-pyrrolizinone (3).

To a stirred mixture of 12.1 g compound (1) and 8 g AlCl₃ in 40 ml tetrachloroethane was added dropwise 5.3 g 4-chlorobenzoyl chloride during 1 hour. The mixture was stirred at 40°–45° C. for 2 hours. The reaction mixture was added into 100 g ice-water. The organic layer was dried over MgSO₄. Evaporated to dryness, 7 g crude product was obtained. Recrystallized from ethanol, 5.5 g of (3) was obtained as a white solid, mp 165°–166.5° C., yield 72%.

¹HNMR (CDCl₃), δ3.15 (t, 2H), 4.37 (t, 2H), 7.09 (S, 1H), 7.53 (d, 2H), 7.64 (m, 1H), 7.74 (d, 2H).

EXAMPLE 4

2-dimethylaminomethyl-5-(4-chlorobezoyl)-1, 2-dihydro-1-pyrrolizinone (4).

A mixture of 10 g compound (3), paraformaldehyde 1.6 g and dimethylamine chloride 4 g in 400 ml benzene was refluxed with stirring for 10 hours. After cooling to room temperature, the mixture was filtered by suction, a solid was obtained. The solid obtained was recrystallized from absolute ethanol, and 13.8 g of (4) was obtained as a white powder, mp 182°–183° C., yield 84%.

¹HNMR (DMSO), δ2.83 (s, 6H), 3.50 (M, 1H), 3.83 (m, 2H), 4.39 (dd, 1H), 478 (dd, 1H), 7.12 (s, 1H), 7.65 (d, 2H), 7.82 (d, 2H), 8.08 (s, 1H).

EXAMPLE 5

2-(4-methylphenyamino)methyl-1, 2-dihydro-1-pyrrolizinone (5).

A solution of 17.5 g, compound (2) and 10 g 4-methylaniline was allowed to stand at room temperature for 12 hours. 22 g yellow solid was obtained after filtering. Recrystallized from ethanol, 19 g (5) was obtained as a white crystal, mp 112°–114° C., yield 83%.

¹HNMR (CDCl₃), δ2.23 (s, 3H), 3.36 (m, 1H), 3.50 (m, 2H), 3.96 (br, 1H), 4.06 (dd, 1H), 4.42 (dd, 1H), 6.53 (m, 1H), 6.60 (d, 2H), 6.74 (m, 1H), 7.02 (m, 1H).

EXAMPLE 6

5-benzoyl-2-(4-methylphenylamino)methyl-1, 2-dihydro-1-pyrrolizinone (6).

Method (a): To a solution of 4.5 g compound (5) and 2.6 g N-methyl-4-methylaniline in 20 ml methane dichloride was added dropwise phosphorus oxychloride at room temperature. Stirred at 35°–40° C. for 3 hours, 10 ml CH₂Cl₂ and 30 g ice-water were added. The organic layer was washed with dilute aqueous Na₂CO₃. Water, and dried over MgSO₄. Evaporated the solvent and recrystallized from ethanol, 5.5 g of (6) was obtained as a pale-yellow crystal, mp 171°–172° C., yield 76%.

Method (b): From Compound (5), (6) was prepared by a similar procedure as described in the preparation of compound (3), yield 78%.

$^1$HNMR (CDCl), δ2.24 (s, 3H), 3.49 (m, 2H), 3.57 (s, 1H), 3.59 (S, 1H), 4.24 (dd, 1H), 4.54 (dd, 1H), 6.61 (d, 2H), 7.02 (d, 2H), 7.10 (m, 1H), 7.46 (d, 2H), 7.61 (s, 1H), 7.75 (d, 2H).

EXAMPLE 7

5-(4-chlorophenylamino)methyl-1, 2-dihydro-1, 2-pyrrolizinone (7).

Compound (1) 3 g was added to a solution of 3.2 g 4-chloroaniline and 5 ml 36% formaldehyde in 30 ml ethanol. 5 ml concentrated HCl was added, and the solution was stirred at room temperature for 5 hours. 10% $Na_2CO_3$ was added until pH10. Filterred by suction, the solid was recrystallized from ethanol, 6 g of (7) was obtained as a white crystal, mp 144°–145° C., yield 92%.

$^1$HNMR (CDCl$_3$), δ2.99 (t, 2H), 4.21 (t, 2H), 4.31 (s, 2H), 6.44 (d, 1H), 6.58 (d, 2H), 6.67 (d, 1H), 7.12 (d, 2H).

EXAMPLE 8

2-Cyanomethyl-1, 2-dihydro-1-pyrrolizinone (8).

To 100 ml $H_2O_0$ were added 8.6% of compound 2 and 5.2 g KCN. The solution was gently heated to 100° C. and kept stirring for 10 minutes. After cooling to r.t., the reaction mixture was extracted with $CH_2Cl_2$ (60×3). Evaporated the solvent, 6 g oil was obtained. Purified by column chromatography on silica gel, 4 g of compound 8 was obtained as white powder, mp 68° C., yield 68%.

$^1$HNMR (CDCl$_3$) δ: 2.72 (m, 1H), 3.03 (m, 1H), 3.43 (m, 1H), 4.18 (m, 1H), 4.65 (m, 1H), 6.58 (t, 1H), 6.82 (t, 1H), 7.11 (d, 1H).

EXAMPLE 9

2-(2-Aminomethyl)-1, 2-dihydro-1-pyrrolizinone (9).

Compound 8 was reduced by hydrogenation catalyzed by Raney-Ni. The reaction was carried out in acetic anhydride-ethanol under ordinary pressure at r.t. Thus, 5 g of compound 8 was dissolved in 50 ml ethanol containing 3.2 g acetic anhydride, and 0.5 g Raney-Ni was added to the solution. After hydrogen uptake ceased, the catalyst was filtered off, and 5 ml $H_2O$ was added to the filtrate. Concentrated by rotatory evaporation, 8 sticky oil was obtained. 100 ml of 10% hydrochloric acid was added to the oil, and the mixture was refluxed for 3 hours. After cooling to room temperature, the reaction solution was adjusted to PH 9 with 10% NaOH. Extracted with $CH_2Cl_2$ (40×3), the extracts was dried over $Na_2SO_4$. Evaporated the solvent, 5.5 g of yellow oil was obtained. The oil was separated by column chromatography (silica gel, $CHCl_3$—$CH_3OH$=100:7), 3 g of compound 9 was obtained as a pale yellow solid, mp 80°–81° C., $^1$HNMR (CD$_3$OD) δ: 1.79 (m, 1H), 2.12 (m, 1H), 2.87 (t, 2H), 3.22 (m, 1H), 4.04 (d, 1H), 4.56 (d, 1H), 6.49 (m, 1H), 6.58 (d, 1H), 7.26 (s, 1H).

EXAMPLE 10

2-(2-N.N-dimethylaminoethyl)-1, 2-dihydro-1-pyrrolizinone (10).

2-(2-Aminoethyl)-1, 2-dihydro-1-pyrrlizinone (9) 5 g was dissolved in 30 ml of 50% $CH_3OH$. 5.5 g $(CH_3)_2SO_4$ and 5% NaOH were added dropwise at 35°–40° C., keeping the reaction solution at PH 7–8. The reaction solution was refluxed for half a hour, and then evaporated most of the $CH_3OH$. After cooling to room temperature, the mixture was filtered, and 5.5 g solid was obtained. Crystallized from petrolene ether, 4.2 g of (10) was obtained as a white powder, mp 73°–75° C. $^1$NMR δ: 2.15 (s, 6H), 2.23 (m, 1H), 2.50 (m, 1H), 3.01 (t, 2H), 3.25 (m, 1H), 4.12 (d, 1H), 4.71 (d, 1H), 6.49 (m, 1H), 6.75 (d, 1H), 7.31 (s, 1H).

EXAMPLE 11

The influence of SFZ-47, 58 on inhibition of acetic acid-induces writhe.

SFZ-47 and SFZ-58 were suspended in 0.5% carboxymethylcellulose (CMC) and administered per os. to female mice of weight 18–24 g. 1 hour later, 0.2 ml of a 0.7% solution of acetic acid was injected to mouse by intraperironeally. The animals were observed during the next 20 min. for writhe. The results showed in Table 1.

TABLE 1

The effects of SFZ-47 and SFZ-58 on mouse writhing induced by acetic acid

| Compound | Dose/LD$_{50}$ | Mice (N) | Numb. of writhing ($\bar{x} \pm SD$) | Rate of inhibition (%) |
|---|---|---|---|---|
| N.S. | | 10 | 17.0 ± 6.8 | |
| SFZ-47 | 1/15 | 10 | 0.7 ± 1.5** | 96 |
| SFZ-58 | 1/10 | 10 | 5.0 ± 4.8** | 71 |
| Ibuprofen | 1/5 | 10 | 4.3 ± 3.9* | 75 |
| Indomethacin | 1/4 | 10 | 2.7 ± 1.5 | 84 |

*P < 0.01 compared with normal saline (N.S.)
**P < 0.01 compared with indomethacin

EXAMPLE 12

The influence of SFZ-47, 58 on inhibition of Carrageenin-Induced Paw Edema in Rat.

The test agent was administered by oral liquid to male rats of weight 140–180 g. 0.05 ml of 1% carrageenin injected into the pad of the right hind paw 1 hour later. The perimeter of the rat ankles were measured each hour after compound administration. The results are listed in Table 2.

TABLE 2

The inhibition of SFZ-47 and SFZ-58 on carrageenin-induced paw edema.

| Compound | Dose/LD | Number of rats | 1 hour | 2 hours | 3 hours | 4 hours | 5 hours |
|---|---|---|---|---|---|---|---|
| N.S. | | 8 | 0.40 ± 0.00 | 0.78 ± 0.09 | 0.75 ± 0.09 | 0.75 ± 0.05 | 0.76 ± 0.09 |
| SFZ-47 | 1/15 | 8 | 0.28 ± 0.01 | 0.39 ± 0.07 | 0.45 ± 0,00 | 0.43 ± 0.10 | 0.46 ± 0.10 |
| SFZ-58 | 1/10 | 8 | 0.27 ± 0.12 | 0.45 ± 0.16 | 0.51 ± 0.12 | 0.46 ± 0.15 | 0.49 ± 0.16 |
| Ibuprofen | 1/5 | 8 | 0.29 ± 0.06 | 0.41 ± 0.11 | 0.52 ± 0.00 | 0.51 ± 0.00 | 0.47 ± 0.10 |
| Indomethacin | 1/4 | 8 | 0.21 ± 0.18 | 0.33 ± 0.08 | 0.45 ± 0.08 | 0.43 ± 0.13 | 0.43 ± 0.13 |

P < 0.05, P < 0.01 compared with indomethacin

The result showed that the analgesic activity of SFZ-47 ($\frac{1}{15}$ LD$_{50}$) was more potent than indomethacin ($\frac{1}{4}$ LD$_{50}$) or ibuprofen ($\frac{1}{10}$ LD$_{50}$). Anti-inflammatory potence was similar.

EXAMPLE 13

Safety.

The compounds are safe because orally LD$_{50}$ of compounds were between 1000–3000 mg/kg in rats.

TABLE 3

Effects of SFZ-47 and SFZ-58 on gastric mucosa of rats

| Compound | Dose (mg/kg) | Number of rats | Ulcer index (mm$^2$) |
|---|---|---|---|
| SFZ-47 | 400 | 5 | 0 |
| SFZ-58 | 300 | 5 | 0 |
| Ibuprofen | 200 | 5 | 13.3 ± 4.2 |
| Indomethacin | 10 | 5 | 14.0 ± 6.9 |

The data of Table 3 showed that SFZ-47 and 58 are more safe than ibuprofen and indomethacin.

The present invention provides new compositions for anti-inflammation and analgesia. This compositions is a safe pharmaceutical agent.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is understood that all matters herein described are to be interpreted as illustrative and not in a limiting sense.

What is claimed as new and desired to be protected by Letters Patent is set forth in the appended claims:

1. Pyrrolizinone compounds having the following chemical formulas:

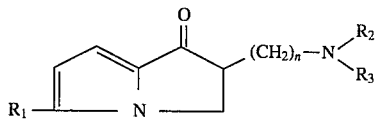
(I)

or

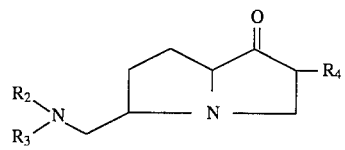
(II)

wherein n is 1–3;

wherein R$_1$ is H, or substituted benzyl group:

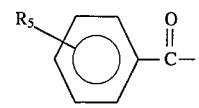

R$_2$ is H, an alkyl group of 1–3 carbon atoms or a substituted phenyl group:

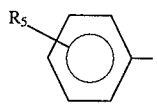

R$_3$ is a group as R$_1$ and R$_2$ defined as above; or R$_3$=—(CH$_2$)n—R$_2$, n=4 or 5 and R$_4$ is H, a substituted benzyl or benzylidene group:

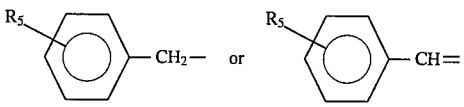

R$_5$ is H, F, Cl, Br, —COOHCH$_3$COO—, H$_3$N—, CH$_3$CONH—, or an alkoxy group of 1–4 carbon atoms.

2. A pharmaceutical composition comprising the salts of organic and inorganic acid and a pharmaceutically acceptable carrier.

3. A method of treating anti-inflammatory disorders according to the analgesic compounds of claim 1.

* * * * *